United States Patent [19]

Bell et al.

[11] Patent Number: 4,714,776

[45] Date of Patent: Dec. 22, 1987

[54] ANTIALLERGIC AGENTS

[75] Inventors: Randy L. Bell, North St. Paul; George G. I. Moore, Woodbury, both of Minn.

[73] Assignee: Riker Laboratories, Inc., St. Paul, Minn.

[21] Appl. No.: 757,686

[22] Filed: Jul. 22, 1985

[51] Int. Cl.[4] .................... C07C 65/32; C07C 69/76
[52] U.S. Cl. .................... 562/460; 560/52; 558/415; 514/544; 514/568
[58] Field of Search .................... 562/460; 560/52; 558/415; 514/544, 568

[56] References Cited

U.S. PATENT DOCUMENTS 4,070,484 1/1978 Harita et al. .................... 424/319
4,172,151 10/1979 Moore .................... 424/330

FOREIGN PATENT DOCUMENTS 1379593 1/1964 France .

OTHER PUBLICATIONS

Sergouskayer, N. L. et al., Zh. Org. Khim 18(10) 2167-70, 1982.
EPO application Publication No. 0 181 568, published 5/21/86.

Primary Examiner—Paul J. Killos
Attorney, Agent, or Firm—Donald M. Sell; James A. Smith; Robert W. Sprague

[57] ABSTRACT

Novel antiallergic agents are described which are carboxy-substituted 3,5-di(tertiary-butyl)-4-hydroxybenzophenones. Pharmaceutical compositions containing and pharmacological methods for using such compounds are also described, as are synthetic intermediates for preparing such compounds.

7 Claims, No Drawings

ANTIALLERGIC AGENTS

TECHNICAL FIELD

This invention relates to novel antiallergic agents. This invention also relates to pharmacological methods for using and pharmaceutical compositions comprising such compounds. This invention further relates to synthetic intermediates for preparing such compounds.

BACKGROUND OF THE INVENTION

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle, but also on other tissues as well. In addition, they promote mucous production, modulate vascular permeability changes and are potent inflammatory mediators in human skin. The most important compound in the second group of leukotrienes, namely dihydroxy fatty acids, is Leukotriene $B_4$. This compound is a potent chemotactic agent for neutrophils and eosionphils and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a lipoxygenase enzyme. See for example, D. M. Bailey et al., *Ann. Rpts. Med. Chem* 17 203 (1982).

RESPIRATORY CONDITIONS

Asthma

The leukotrienes are potent spasmogens of human trachea, bronchus and lung parenchymal strips, and when adminstered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. Lipoxygenase products are also thought to be regulators of mast cell degranulation and recent studies with human lung mast cells have suggested that lipoxygenase inhibitors (but not corticosteroids) may suppress antigen induced mast cell degranulation. In vitro studies have shown that antigen challenge of human lung results in the release of leukotrienes and that, in addition, purified human mast cells can produce substantial amounts of leukotrienes. There is therefore good evidence that the leukotrienes are important mediators of human asthma. Lipoxygenase inhibitors would therefore be a new class of drugs for the treatment of asthma. See, for example, B Samuelsson, *Science*, 220 568–575 (1983).

SKIN DISEASES

Psoriasis

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in non-involved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, to modulate mucous production and mucociliary clearance, and to mediate the accumulation of inflammatory leukocytes.

Leukotrienes can also mediate other diseases. These include atopic dermatitis, gouty arthritis, gall bladder spasms and ulcerative colitis. In addition they may have a role in cardiovascular disease because Leukotrienes $C_4$ and $D_4$ act as coronary and cerebral arterial vasoconstrictors and these compounds may also have negative inotropic effects on the myocardium. In addition, the leukotrienes are important mediators of inflammatory disease through their ability to modulate leukocyte and lymphocyte function.

Many substituted di-t-butylphenols are known. Generally these compounds may be useful as antioxidants. Some of these compounds are also known to be active anti-inflammatory agents. Compounds wherein 2,6-di-t-butylphenol is substituted in the 4 position by an unsubstituted phenyl or certain simply-substituted phenyls are known as anti-inflammatory agents. See, for example, U.S. Pat. No. 4,172,151 and reference cited therein.

No compounds wherein a 2,6-di-t-dibutylphenol is substituted in the 4 position by a benzoyl group wherein such benzoyl group is substituted by a moiety including a carboxy group are known.

SUMMARY OF THE INVENTION

This invention relates to certain di-t-butylphenols containing a benzoyl group which is carboxy-functional. These compounds are useful as inhibitors of mammalian leukotriene biosynthesis. As such, these compounds are useful therapeutic agents for treating allergic conditions, particularly asthma. Pharmaceutical compositions comprising such compounds, pharmacological methods of using such compounds, and synthetic intermediates for preparing such compounds are also described.

DETAILED DESCRIPTION OF THE INVENTION

The present invention relates to novel antiallergic compounds of Formula I:

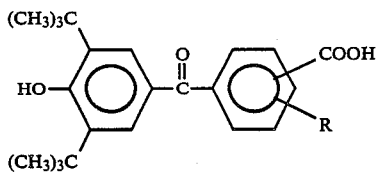

wherein R is hydrogen, lower alkyl, lower alkoxy or chloro; and carboxylate derivatives thereof selected from lower alkyl esters, (lower)alkylamino(lower)alkyl esters, pharmaceutically acceptable (lower)alkylamino(lower)alkyl ester acid-addition salts and pharmaceutically acceptable carboxylate salts. This invention also relates to pharmacological methods for using such compounds and pharmaceutical compositions containing such compounds.

By "lower" as used in connection with "alkyl" and "alkoxy", it is meant that such groups contain one to about four carbon atoms. Most preferred alkyl groups contain one or two carbon atoms.

It is well known to the art that pharmaceutically acceptable salts such as alkali metal, alkaline earth, aluminum and other metal and amine salts of pharmaceutically active acids are the equivalents of the acids in terms of activity, and in some cases may even offer advantages in absorption, formulation and the like. Pharmaceutically-acceptable carboxylate salts of the compounds of the invention which contain carboxyl are prepared by reaction of the acid with a base and subsequent evaporation to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of Formula I include the esters and alkylaminoalkyl ester salts thereof. In the ester derivatives, the hydrogen portion of the carboxylic acid group is replaced with an alkyl or substituted alkyl, preferably an alkylaminoalkyl group.

Esters of the compounds of the invention may be obtained as intermediates during the preparation of the acidic compound. In some cases, the esters may be prepared directly using standard synthetic methods. These esters may exhibit antiallergic activity, but they are primarily of interest as synthetic intermediates, although in some instances hydrolyzable or salt-forming esters may be of interest as thereapeutic agents. Preferred esters are alkyl esters and alkylaminoalkyl esters having one to four carbon atoms in the alkyl group. Especially preferred are alkylaminoalkyl esters such as the dimethylaminoethyl esters which will form salts, e.g., hydrochlorides.

Ester derivatives may be obtained by alkylation of an alkali metal salt of the compound in dimethylformamide with an alkyl iodide or dialkylaminoalkylchloride.

Compounds of the invention wherein —COOH is oriented para to the

are presently preferred.

The compounds of the invention are readily prepared by Scheme I below wherein R is as defined above:

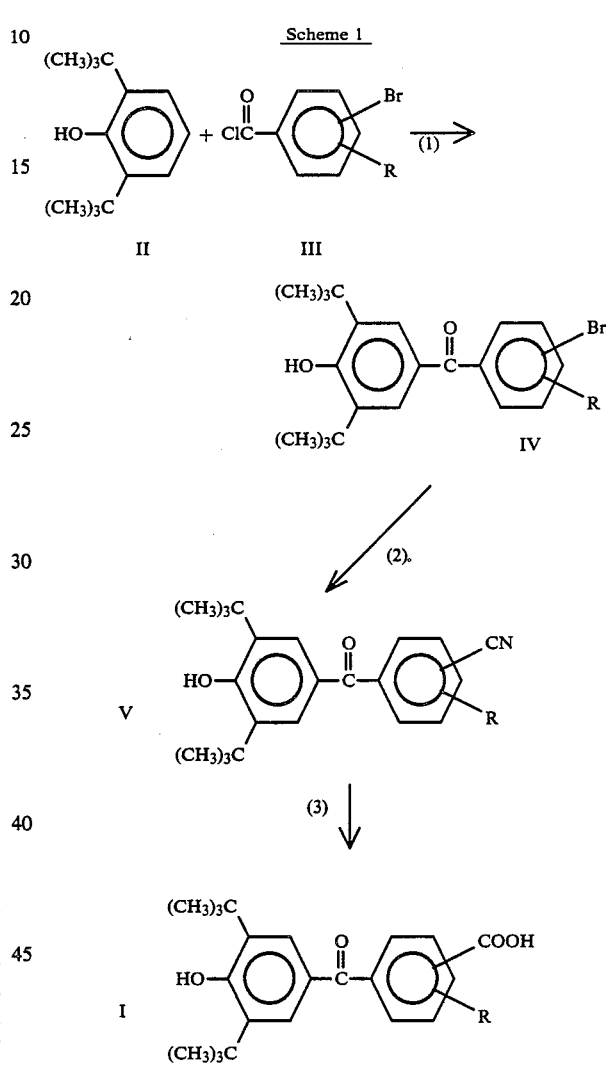

The reaction of step (1) is a standard Friedel-Crafts reaction of known 2,6-di(tertiary-butyl)phenol (II) and a bromobenzoyl chloride of Formula III in the presence of a strong Lewis acid such as aluminum chloride or titanium tetrachloride as a catalyst. The bromobenzyl chlorides of Formula III are known or may be prepared by conventional methods from the corresponding bromobenzoic acids. The intermediates of Formula IV are novel.

The reaction of step (2) involves heating an intermediate of Formula IV with a metal cyanide salt, preferably cuprous cyanide, in a solvent such as pyridine, N-methylpyrrolidone or quinoline to provide a novel intermediate of Formula V.

The reaction of step (3) involves the hydrolysis of the cyano group of the compound of Formula V to a carboxyl group to provide compounds of Formula I. This hydrolysis reaction can be carried out using acid or base. Hydrolysis using an excess of a moderately concentrated aqueous inorganic base such as sodium hydroxide is preferred. The mixture is diluted with a solvent which is suitable to effect dissolution of the intermediate of Formula V such as a lower alcohol. The mixture is then heated at its reflux temperature until the intermediate of Formula V has been reacted. The products of Formula I are readily isolated by conventional methods.

The antiallergic biological activity of the compounds of Formula I may be demonstrated via a variety of assays including in vitro assays for measuring inhibition of lipoxygenase activity and leukotriene synthesis, and in vivo assays for inhibiting bronchoconstriction.

More specifically, a suitable assay for demonstrating inhibition of lipoxygenase activity by the compounds of Formula I utilizes lipoxygenase isolated from mammalian lung tissue, for example, the lung tissue of guinea pigs. An example of such an assay is that described by Ben Aziz, et al., Anal. Biochem. 34, 88 (1970), incorporated herein by reference. The inhibition of lipoxygenase activity is measured by a rapid and sensitive spectrophotometric technique. Compounds of Formula I exhibit an $IC_{50}$ (concentration at which 50% of the activity is inhibited) of less than about 100 micromolar.

The activity of the compounds of Formula I may also be demonstrated in a more specific test for leukotriene inhibition. This test utilizes the cell free leukotriene biosynthesis system of M. Steinhoff et al. Biochim. Biophys. Acta. 68, 28 (1980), incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhause et al. FEBS Letter 146, 111-114. Drugs are dissolved in ethanol or dimethyl sulfoxide and preincubated for five minutes. Phenidone is used as a positive control. The compounds of Formula I exhibit an $IC_{50}$ of less than 100 micromolar.

The compounds of Formula I are relatively inactive as inhibitors of cyclooxygenase. This is an important property in order for there to be good in vivo antiallergic activity. A convenient in vitro method for measuring cyclooxygenase inhibition is an assay wherein the amount of thromboxane B2 production is measured in a whole human bloodclotting assay. The thromboxane B2 production is measured by a radioimmunoassay as described by Patrons et al., Thromb. Res. 17, 317 (1980), incorporated herein by reference. The compounds of Formula I do not show appreciable activitiy at concentrations of 100 micromolar or less when tested in this assay.

The in vivo test used to demonstrate antiallergic activity of the compounds of Formula I may be any of those known to those skilled in the art. Preferably, bronchoconstriction in sensitized guinea pigs is measured upon antigen challenge. This test is described in broad terms by Piechuta et al., Immunology, 38, 385 (1979), incorporated herein by reference, and more specifically by Hammerbeck and Swingle, Int. Archs. Allergy Appl. Immun. 74, 84–90 (1984), incorporated herein by reference. It is used in a modified form as follows: Male Hartley guinea pigs (250–600 g) which are pretreated with an antihistamine, for example, chlorpheniramine, and then dosed intraperitoneally with compound of the invention (5–40 mg/kg) 15 minutes prior to challenge or orally 30 minutes prior to challenge, are aerosol challenged with either water or ovalbumin at a concentration of 10 mg per ml. The animals are placed under an inverted dessicator jar (18 × 14 cm) with a constant flow of air coming into the chamber from a compressed-air source to prevent hypoxia. Air flow leaving the chamber and fluctuations due to respiration are monitored through a separate outlet with a Fleisch No. 0000 pneumotachograph (available from Beckman Instruments, Inc., Schiller Park, Ill.) coupled to a Beckman Type R dynograph (available from Beckman Instruments, Inc.) Aerosolization through a third outlet is made via a No. 4 DeVilbiss nebulizer (available from The Devilbiss Company, Somerset, PA) for 90 seconds at 150 mm Hg. The characteristic respiratory patterns observed are summations of two air exchange processes occurring simultaneously in the chamber. One exchange process is due to inspiration and expiration of air into and out of the animal, while the other exchange process is due to the air flow into and out of the chamber due to respiratory movements. The tracing obtained is the mechanical representation of the summation of those flows. Superimposed on the tracings is a characteristic spiking ("notching"), which appears to be an exaggerated expiratory movement, the frequency of which correlates with the severity of the bronchoconstrictive reaction. The frequency of notching for 15-minute periods beginning 4 minutes after the beginning of the aerosol challenge is used for comparing various treatments. Effects are considered significant if the t value achieved $p < 0.05$. The compounds of Formula I exhibit an intraperitoneal or oral $ED_{40}$ of 100 mg per kg or less when tested in the above model.

Thus, compounds of Formula I are antiallergic agents exhibiting in vivo activity in mammals. The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form, and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions, capsles, including delayed or sustained release dosage forms. Dosage forms for administration by inhalation include aerosols and sprays which may be administered in metered doses if desired.

For treating allergies or allergic reactions, the compound of Formula I may be administered by any conventional mode, for example, orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area salves, patches, controlled release patches, emulsions, etc. are convenient dosage forms.

For treating cardiovascular conditions any suitable mode of administration may be used.

In addition to the common dosage forms listed above, the compounds of Formula I may also be administered for various utilities and indications or for inhibiting leukotriene synthesis by conventional controlled release means and/or delivery devices.

In preparing suitable dosage forms, conventional compounding procedures and ingredients, for example, diluents, carriers, etc. may be used. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water, and the like. Similarly, the carrier or diluent can include any time delay material well known to the art, such as glyceryl monostearate or glyceryl distearate, these being useful alone or, for example, in combination with wax.

The following examples are provided to illustrate the invention, but at not intended to limit the invention.

EXAMPLE 1

Synthesis of 4'-Carboxy-3,5-di(tertiary-butyl)-4-hydroxybenzophenone

PART A

A mixture of 100 g (0.497 mole) of 4-bromobenzoic acid and 100 g of thionyl chloride in 300 ml of dichloromethane containing a few drops of N,N-dimethylformamide was heated at reflux for two days. The low boiling liquid were then removed by evaporation, and the remaining liquid was distilled to provide 4-bromobenzoyl chloride.

To a stirred solution of 107 g (0.487 mole) of 4-bromobenzoyl chloride in about 200 ml of carbon disulfide was added first 66 g (0.50 mole) of aluminum chloride in small portions, and then, over one hour, a solution of 100.7 g (0.487 mole) of 2,6-di(tertiary-butyl)-phenol in carbon disulfide. The mixture was stirred for about 16 hours, and was then evaporated and extracted with dichloromethane. The extracts were washed with 10% hydrochloric acid, dried over magnesium sulfate, and evaporated. The residue crystallized and was washed with hexane. Recrystallization from hexane provided crystals of 4'-bromo-3,5-di(tertiary-butyl)-4-hydroxybenzophenone, m.p. 170°–172.5° C. Analysis: Calculated for $C_{21}H_{25}BrO_2$: %C, 64.8; %H, 6.5; Found: %C, 65.1; %H, 6.6

PART B

A stirred mixture of 52 g (0.13 mole) of 4'-bromo-3,5-di(tertiary-butyl)-4-hydroxybenzophenone, 20 g (0.22 mole) of cuprous cyanide and 150 ml of quinoline was heated at about 180° C. for one day, followed by heating at reflux (235° to 245° C.) for two hours. The cooled solution was mixed with about one liter of 10% aqueous hydrochloric acid, and 400 ml of dichloromethane was added. The solid was separated by filtration, and extracted with additional hydrochloric acid and dichloromethane. The filtrates and washings were combined and the organic layer was separated and evaporated. The residue was recrystallized from a benzene-hexane mixture with treatment with decolorizing charcoal to provide 4'-cyano-3,5-di(tertiary-butyl)-4-hydroxybenzophenone. A further recrystallization from a mixture of ethanol and isopropanol with treatment with decolorizing charcoal provided white needles, m.p. 166.5° to 168° C. Analysis: Calculated for $C_{22}H_{25}NO_2$: % C, 78.8; %H, 7.5; %N, 4.2; Found; %C, 78.8; %H, 7.5; %N, 4.1.

PART C

A mixture of 3.35 g (0.010 mole) of 4'-cyano-3,5-di(tertiary-butyl)-4-hydroxybenzophenone, 25 ml of 20% aqueous sodium hydroxide solution and 25 ml of ethanol was heated at its reflux temperature for about 16 hours. The solution was extracted and washed twice with dichloromethane. The aqueous portion was poured into cold dilute hydrochloric acid and a white solid precipitated. The solid was collected by filtration and was washed with water. The solid was recrystallized from about 50 ml of ethanol with treatment with decolorizing charcoal to provide white solid 4'-carboxy-3,5-di(tertiary-butyl)-4-hydroxybenzophenone, m.p. 248.5°250.5° C. Analysis: Calculated for $C_{22}H_{26}O_4$: %C, 74.6; %H, 7.4; Found: %C, 74.7; %H, 7.5.

EXAMPLE 2

Synthesis of 2'-carboxy-3,5-di(tertiary-butyl)-4-hydroxybenzophenone.

PART A

To a mixture of 50.2 g (0.25 mole) of 2-bromobenzoic acid in 200 ml of 1,2-dichloroethane was added 13.7 g (0.10 mole) of phosphorous trichloride in 100 ml of dichloroethane. The mixture was heated at reflux for 4 hours to provide 2-bromobenzoyl chloride.

To the above solution of 2-bromobenzoyl chloride was added 51.6 g (0.25 mole) of 2,6-di(tertiary-butyl)-phenol. The resulting solution was then added dropwise over one hour to 47.4 g (0.25 mole) of titanium tetrachloride in 100 ml of dichloroethane. The mixture was heated at reflux for one hour, 400 ml of 20% hydrochloric acid was added and the organic layer was separated. The organic layer was washed sequentially with water, sodium bicarbonate solution and water again, and was then evaporated. The residue was triturated with hexane and scratched to initiate crystallization. The solid 2'-bromo-3,5-di(tertiary-butyl)-4-hydroxybenzophenone was recrystallized from isopropyl alcohol with treatment with decolorizing charcoal to provide white solid, m.p. 149°–150.5° C. Analysis; Calculated for $C_{21}H_{25}BrO_2$: %C, 64.8; %H, 6.5; Found: %C, 64.7; %H, 6.5.

PART B

A stirred mixture of 3.89 g (0.010 mole) of 2'-bromo-3,5-di(tertiary-butyl)-4-hydroxybenzophenone, 1.97 g (0.022 mole) of cuprous cyanide and 30 ml of pyridine was heated at its reflux temperature under a nitrogen atmosphere for about 16 hours. The mixture was cooled and diluted and neutralized with 10% hydrochloric acid, followed by addition of 100 ml of dichloromethane. The solids were removed by filtration and the organic layer was separated and washed with water. Drying and evaporation of the organic layer provided a residue which was washed with benzene and hexane, then scratched to initiate crystallization. The product was tan crystals of 2'-cyano-3,5-di(tertiary-butyl)-4-hydroxybenzophenone, m.p. 103.5°–105° C. Analysis: Calculated for $C_{22}H_{25}NO_2$: %C, 78.8; %H, 7.5; %N, 4.2; Found: %C, 78.9; %H, 7.7; %N, 4.1.

PART C

Using the method of Example 1, Part C, 2'-cyano-3,5-di(tertiary-butyl)-4-hydroxybenzophenone, was converted to a white solid which was recrystallized from 1:3 benzene:hexane to provide 2'-carboxy-3,5-di(tertiary-butyl)-4-hydroxybenzophenone, m.p. 173°–174.5° C. Analysis: Calculated for $C_{22}H_{26}O_4$: %C, 74.6; %H, 7.4; Found: %C, 75.2; %H, 7.5.

EXAMPLES 3-6

Intermediates of Formula IV of the invention which could be prepared from known bromobenzoic acids using the general method of Part A of Examples 1 and 2 are shown in Table I.

TABLE I

| Example No. | Starting Material | Compound of Formula IV |
|---|---|---|
| 3 | Br-substituted HO$_2$C-phenyl | (CH$_3$)$_3$C, HO, (CH$_3$)$_3$C substituted benzophenone with Br |
| 4 | HO$_2$C-phenyl-Br with CH$_3$ | (CH$_3$)$_3$C, HO, (CH$_3$)$_3$C substituted benzophenone with Br and CH$_3$ |
| 5 | Br, HO$_2$C, OCH$_3$ phenyl | (CH$_3$)$_3$C, HO, (CH$_3$)$_3$C benzophenone with Br and OCH$_3$ |
| 6 | Cl, HO$_2$C, Br phenyl | (CH$_3$)$_3$C, HO, (CH$_3$)$_3$C benzophenone with Cl and Br |

EXAMPLES 7-10

Using the general method of Part B of Examples 1 and 2, the bromo intermediates indicated in Table II could be converted to the nitrile intermediates which are also indicated in Table II.

TABLE II

| Example No. | Intermediate of Formula IV | Intermediate of Formula V |
|---|---|---|
| 7 | Example 3 | (CH$_3$)$_3$C, HO, (CH$_3$)$_3$C benzophenone with CN |
| 8 | Example 4 | (CH$_3$)$_3$C, HO, (CH$_3$)$_3$C benzophenone with CN and CH$_3$ |
| 9 | Example 5 | (CH$_3$)$_3$C, HO, (CH$_3$)$_3$C benzophenone with CN and OCH$_3$ |
| 10 | Example 6 | (CH$_3$)$_3$C, HO, (CH$_3$)$_3$C benzophenone with Cl and CN |

EXAMPLES 11-14

Using the method of Example 1, Part C, the nitrile intermediates indicated in Table III could be converted to the compounds of Formula I shown in Table III.

TABLE III

| Example No. | Intermediate of Formula V | Product of Formula I |
|---|---|---|
| 11 | Example 7 | (CH$_3$)$_3$C, HO, (CH$_3$)$_3$C benzophenone with COOH |
| 12 | Example 8 | (CH$_3$)$_3$C, HO, (CH$_3$)$_3$C benzophenone with COOH and CH$_3$ |
| 13 | Example 9 | (CH$_3$)$_3$C, HO, (CH$_3$)$_3$C benzophenone with COOH and OCH$_3$ |
| 14 | Example 10 | (CH$_3$)$_3$C, HO, (CH$_3$)$_3$C benzophenone with Cl and COOH |

What is claimed is:

1. A compound of the formula

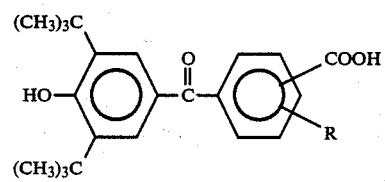

wherein R is hydrogen, lower alkyl, lower alkoxy or chloro; or a derivative thereof selected from a lower alkyl ester, a (lower)alkylamino(lower)alkyl ester, a pharmaceutically acceptable (lower)alkylamino(lower-)alkyl ester acid-addition salt and a pharmaceutically acceptable carboxylate salt.

2. A compound according to claim 1, wherein the carboxyl is oriented para to the carbonyl.

3. A compound of the formula

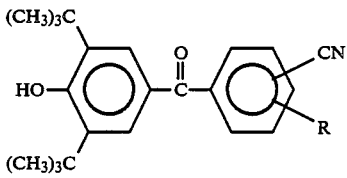

wherein R is hydrogen, lower alkyl, lower alkoxy or chloro.

4. A method for inhibiting bronchoconstriction due to an allergic reaction in a mammal comprising administering a compound to said mammal in an amount effective to inhibit said bronchoconstriction, said compound being of the formula:

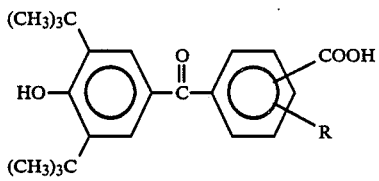

wherein R is hydrogen, lower alkyl, lower alkoxy or chloro; or a derivative thereof selected from a lower alkyl ester, a (lower)alkylamino(lower)alkyl ester, a pharmaceutically acceptable (lower)alkylamino(lower-)alkyl ester acid-addition salt and a pharmaceutically acceptable carboxylate salt.

5. An antiallergic pharmaceutical composition comprising an antiallergic compound and a pharmaceutically acceptable carrier, said antiallergic compound being present in an amount sufficient for providing an antiallergic response and being of the following formula:

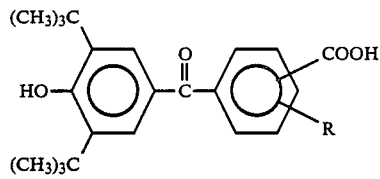

wherein R is hydrogen, lower alkyl, lower alkoxy or chloro; or a derivative thereof selected from a lower alkyl ester, a (lower)alkylamino(lower)alkyl ester, a pharmaceutically acceptable (lower)alkylamino(lower-)alkyl ester acid-addition salt and a pharmaceutically acceptable carboxylate salt.

6. A method for inhibiting leukotriene synthesis in a mammal comprising administering a compound to said mammal in an amount effective to inhibit said synthesis, said compound being of the formula:

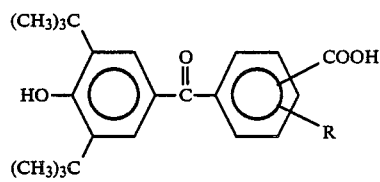

wherein R is hydrogen, lower alkyl, lower alkoxy or chloro; or a derivative thereof selected from a lower alkyl ester, a (lower)alkylamino(lower)alkyl ester, a pharmaceutically acceptable (lower)alkylamino(lower-)alkyl ester acid-addition salt and a pharmaceutically acceptable carboxylate salt.

7. A method for inhibiting lipoxygenase activity in a mammal comprising administering a compound to said mammal in an amount effective to inhibit said activity, said compound being of the formula:

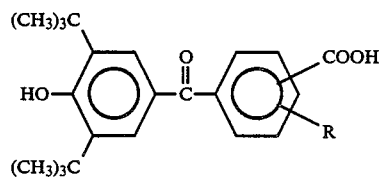

wherein R is hydrogen, lower alkyl, lower alkoxy or chloro; or a derivative thereof selected from a lower alkyl ester, a (lower)alkylamino(lower)alkyl ester, a pharmaceutically acceptable (lower)alkylamino(lower-)alkyl ester acid-addition salt and a pharmaceutically acceptable carboxylate salt.

* * * * *